United States Patent [19]

Bose et al.

[11] Patent Number: 5,681,691
[45] Date of Patent: Oct. 28, 1997

[54] PHOTOGRAPHIC ELEMENT CONTAINING AN IMPROVED PYRAZOLOTRIAZOLE COUPLER

[75] Inventors: Judith A. Bose, Webster; Louis E. Friedrich; David Hoke, both of Rochester; Joan C. Potenza, Rush; Robert F. Romanet, Rochester; Stephen P. Singer, Spencerport; Ronald R. Valente, Fairport, all of N.Y.

[73] Assignee: Eastman Kodak Company, Rochester, N.Y.

[21] Appl. No.: 725,811

[22] Filed: Oct. 4, 1996

Related U.S. Application Data

[63] Continuation-in-part of Ser. No. 570,054, Dec. 11, 1995, abandoned.
[51] Int. Cl.$^6$ .................................................. G03C 7/38
[52] U.S. Cl. .................................................. 430/558
[58] Field of Search .................................................. 430/558

[56] References Cited

U.S. PATENT DOCUMENTS

| | | | |
|---|---|---|---|
| 5,302,496 | 4/1994 | Romanet et al. | 430/558 |
| 5,387,500 | 2/1995 | Ling et al. | 430/558 |

*Primary Examiner*—Lee C. Wright
*Attorney, Agent, or Firm*—Arthur E. Kluegel

[57] ABSTRACT

The invention provides a photographic element comprising a light sensitive silver halide emulsion layer having associated therewith a dye-forming coupler having formula I:

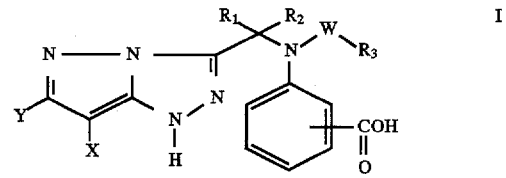

wherein $R_1$ is selected from the group consisting of alkyl, aryl, and heterocyclic groups;

$R_2$ is selected from the group consisting of hydrogen, alkyl, aryl, and heterocyclic groups;

W is C(O) or S(O)$_2$;

$R_3$ is selected from the group consisting of alkyl and aryl groups having a calculated logP of at least 9;

Y is a substituent; and

X is H or a coupling-off group.

20 Claims, No Drawings

PHOTOGRAPHIC ELEMENT CONTAINING AN IMPROVED PYRAZOLOTRIAZOLE COUPLER

CROSS-REFERENCE TO RELATED APPLICATION

This application is a continuation-in-part of U.S. Ser. No. 08/570,054, filed Dec. 11, 1995, abandoned.

FIELD OF THE INVENTION

This invention relates to an improved photographic element that contains a pyrazolotriazole magenta dye-forming coupler that exhibits improved pH sensitivity during processing of the element.

BACKGROUND OF THE INVENTION

It is well-known to use pyrazolotriazole couplers for forming magenta dyes in photographic elements. One type of coupler used for this purpose is a 1-H-pyrazolo(5,1-c)-1,2,4-triazole coupler. An example of such a coupler is shown in Romanet et al. U.S. Pat. No. 5,183,728. The couplers shown in the Romanet patent contain a nitrogen in a position beta to the carbon in the 3-position of the pyrazolotriazole nucleus. The preferred coupler of the Romanet patent is shown as Compound V at column 25 of the patent. This compound corresponds to comparative coupler C-1 in the present application.

The couplers of the Romanet patent were found to exhibit a desired level of reactivity and to produce a dye having a very satisfactory hue. However, the coupler of Romanet has been found to have an undesirable sensitivity to the pH of the developer solution used when processing a photographic element containing the coupler to develop an image. The result is that the relationship between the amount of exposure and the resulting dye density (the D-LogE curve or gamma) varies for the coupler as a function of the pH of the processing solution.

It is, of course, essential that a photographic element having a particular latent image produce the same resulting viewable image upon development regardless of the minor variations in the maintenance of the target pH values in the developer solution that are typical in the processing business.

Moreover, the couplers of Romanet should contain water-solubilizing groups in order to have high reactivity towards oxidized developer. This results in high imaging efficiency. However, these same substituents also cause the couplers to partially or totally dissolve at the high pH of the developer solution and diffuse (wander) into other imaging layers where it can react with the oxidized developer generated in that layer. This leads to undesirable color contamination. Reducing the degree of water solubility of the coupler can minimize coupler wandering but also decreases the ability of the coupler to react with oxidized developer.

Thus, it is a problem to be solved to provide a photographic element which contains a magenta dye-forming coupler which is much less sensitive to variations in the pH value of developer solution than is the case with elements containing couplers previously known while maintaining high imaging efficiency and without color contamination due to coupler wandering.

SUMMARY OF THE INVENTION

The invention provides a photographic element comprising a light sensitive silver halide emulsion layer having associated therewith a dye-forming coupler having formula I:

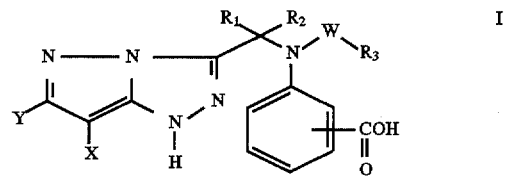

wherein
$R_1$ is selected from the group consisting of alkyl, aryl, and heterocyclic groups;
$R_2$ is selected from the group consisting of hydrogen, alkyl, aryl, and heterocyclic groups;
W is $C(O)$ or $S(O)_2$;
$R_3$ is selected from the group consisting of alkyl or aryl groups having a calculated logP of at least 9;
Y is a substituent; and
X is H or a coupling-off group.

The photographic element is much less sensitive to variations in the pH value of developer solutions than is the case with elements containing couplers previously known.

DETAILED DESCRIPTION OF THE INVENTION

The coupler employed in the element of the invention may be described as a 1-H-pyrazolo(5,1-c)-1,2,4-triazole coupler. The present invention, however, is focused on such a coupler having a particular type of substituent at the three position of the pyrazolotriazole nucleus.

The coupler of the invention may be represented by Formula I, as shown in the Summary of the Invention. The substituent $R_1$ may be an alkyl, aryl, or heterocyclic group. Suitably it is an alkyl or aryl group and is typically selected to be an unsubstituted alkyl or aryl group.

$R_2$ may broadly be hydrogen, alkyl, aryl, or a heterocyclic group. It is suitably hydrogen or an alkyl group and most typically hydrogen. It is possible for $R_1$ and $R_2$ to join to form a carbocyclic or heterocyclic ring.

$R_3$ may be an alkyl or aryl group. The group contains lipophobic properties such that the calculated logP or $\pi$ of the $R_3$ substituent is at least 9 as determined in accordance with MedChem software, Version 3.54, Medicinal Chemistry Project, available from Pomona College, Claremont, Calif. Values for logP or $\pi$ are also available from C. Hansch and A. J. Leo, "Substituent Constants for Correlation Analysis in Chemistry and Biology", Wiley, N.Y. (1979).

The logP of the $R_3$ substituent in accordance with the invention is at least 9, preferably at least 10 and, most preferably, at least 11. Typically, an alkyl group is used with the group containing 18 or more aliphatic carbon atoms.

The —COOH or carboxy group on the anilino ring attached to the alpha carbon at the 3-position of the coupler nucleus may be at any place on the ring with the meta and para position preferred. The meta position is typically suitable.

The nitrogen substituent is the group —W—$R_3$ where W is a carbonyl or sulfonyl group. The carbonyl group is typically preferred for reasons of manufacturing simplicity.

The group Y is suitably an alkyl, aryl, amino, oxy, or a heterocyclic group. Alkyl, aryl, oxy and acylamino groups are typically useful with lower alkyl groups ($C_6$ or less) such as methyl or α-branched alkyl particularly suitable.

The group X may be hydrogen or any known coupling-off group. Halogen, aryloxy, arylthio, alkylthio, and heterocyclic groups are examples. Halogen and aryloxy are typically employed.

In a preferred embodiment, a coupler of formula II is employed:

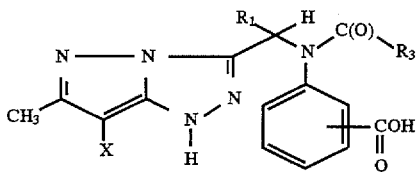

where X, $R_1$, and $R_3$ are as defined above.

More preferably, the coupler has formula II wherein X is as defined above, $R_1$ is an alkyl or aryl group, and $R_3$ is an alkyl group of at least 18 carbon atoms.

Typical examples of couplers useful in accordance with the invention are described with reference to Tables Ia and Ib. Both tables need to be referred to in order to identify all of the substituents for an exemplified coupler.

TABLE Ia

Formula I

| Example | Y | X | W | Acid Position |
|---|---|---|---|---|
| Mag-1 | $CH_3$ | Cl | C=O | meta |
| Mag-2 | t-Bu | Cl | C=O | meta |
| Mag-3 | $CH_3$ | Cl | C=O | meta |
| Mag-4 | $CH_3$ | Cl | C=O | meta |
| Mag-5 | $CH_3$ | $SCH_2CH_2COOH$ | C=O | ortho |
| Mag-6 | $CH_3$ | Cl | C=O | meta |
| Mag-7 | $CH_3$ | Cl | C=O | meta |
| Mag-8 | t-Bu | Cl | C=O | meta |
| Mag-9 | $CH_3$ | Cl | C=O | meta |
| Mag-10 | t-Bu | Cl | C=O | para |
| Mag-11 | $CH_3$ | Cl | C=O | meta |
| Mag-12 | $CH_3O$ | Cl | C=O | meta |
| Mag-13 | $CH_3$ | Cl | $SO_2$ | meta |
| Mag-14 | $CH_3$ | OPh | C=O | meta |
| Mag-15 | O‖t-BuCNH | Cl | C=O | para |

TABLE Ib

| Example | $R_1$ | $R_2$ | $R_3$ |
|---|---|---|---|
| Mag-1 | $CH_3$ | H | $C_{21}H_{43}$ |
| Mag-2 | $CH_3$ | H | $C_{21}H_{43}$ |
| Mag-3 | —$CH_2CH_2OCH_2CH_2$— | | $C_{21}H_{43}$ |
| Mag-4 | —$CH_2CH_2CH_2CH_2CH_2$— | | $C_{19}H_{39}$ |
| Mag-5 | $CH_3$ | H | $C_{21}H_{43}$ |
| Mag-6 | $CH_3$ | H | —CHO—C6H4—C(CH3)3 / $C_{12}H_{25}$ |
| Mag-7 | $CH_3$ | H | —CHO—C6H4—$C_{15}H_{31}$ / $C_4H_9$ |
| Mag-8 | Ph | H | $C_{21}H_{43}$ |
| Mag-9 | Ph | H | $C_{19}H_{39}$ |
| Mag-10 | Ph | H | $C_{19}H_{39}$ |
| Mag-11 | $CH_3CH_2$ | H | $C_{21}H_{43}$ |
| Mag-12 | $CH_3CH_2$ | H | $C_{19}H_{39}$ |
| Mag-13 | $CH_3$ | H | —C6H4—NHC(O)$C_{21}H_{43}$ |
| Mag-14 | Ph | H | $C_{21}H_{43}$ |
| Mag-15 | $CH_3$ | H | $C_{19}H_{39}$ |

Bu = butyl
Ph = phenyl

Unless otherwise specifically stated, substituent groups that may be substituted on molecules herein include any groups, whether substituted or unsubstituted, that do not destroy properties necessary for photographic utility. When the term "group" is applied to the identification of a substituent containing a substitutable hydrogen, it is intended to encompass not only the substituent's unsubstituted form, but also its form further substituted with any group or groups as herein mentioned. Suitably, the group may be halogen or may be bonded to the remainder of the molecule by an atom of carbon, silicon, oxygen, nitrogen, phosphorous, or sulfur. The substituent may be, for example, halogen, such as chlorine, bromine or fluorine; nitro; hydroxyl; cyano; carboxyl; or groups which may be further substituted, such as alkyl, including straight or branched chain alkyl, such as methyl, trifluoromethyl, ethyl, t-butyl, 3-(2,4-di-t-pentylphenoxy)propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy) ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentylphenoxy)acetamido, alpha-(2,4-di-t-pentylphenoxy) butyramido, alpha-(3-pentadecylphenoxy)-hexanamido, alpha-(4-hydroxy-3-t-butylphenoxy)-tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl) carbonylamino, p-dodecyl-phenylcarbonylamino, p-toluylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-toluylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-toluylsulfonamido, p-dodecylbenzenesulfonamido, N-methyltetradecylsulfonamido, N,N-dipropyl-sulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl; N-[3'-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy) acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-toluylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsutfinyl, and p-toluylsulfinyl; thio, such as ethylthio, octylthio, benzylthio, tetradecylthio, 2-(2,4-di-t-pentylphenoxy) ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1-(N-phenylimido)ethyl, N-succinimido or 3-benzylhydantoyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy.

If desired, the substituents may themselves be further substituted one or more times with the described substituent groups. The particular substituents used may be selected by those skilled in the art to attain the desired photographic properties for a specific application and can include, for example, hydrophobic groups, solubilizing groups, blocking groups, releasing or releasable groups, etc. Generally, the above groups and substituents thereof may include those having up to 48 carbon atoms, typically 1 to 36 carbon atoms and usually less than 24 carbon atoms, but greater numbers are possible depending on the particular substituents selected.

The materials of the invention can be used in any of the ways and in any of the combinations known in the art. Typically, the invention materials are incorporated in a silver halide emulsion and the emulsion coated as a layer on a support to form part of a photographic element. Alternatively, unless provided otherwise, they can be incorporated at a location adjacent to the silver halide emulsion layer where, during development, they will be in reactive association with development products such as oxidized color developing agent. Thus, as used herein, the term "associated" signifies that the compound is in the silver halide emulsion layer or in an adjacent location where, during processing, it is capable of reacting with silver halide development products.

To control the migration of various components, it may be desirable to include a high molecular weight hydrophobe or "ballast" group in coupler molecules. Representative ballast groups include substituted or unsubstituted alkyl or aryl groups containing 8 to 48 carbon atoms. Representative substituents on such groups include alkyl, aryl, alkoxy, aryloxy, alkylthio, hydroxy, halogen, alkoxycarbonyl, aryloxcarbonyl, carboxy, acyl, acyloxy, amino, anilino, carbonamido, carbamoyl, alkylsulfonyl, arylsulfonyl, sulfonamido, and sulfamoyl groups wherein the substituents typically contain 1 to 42 carbon atoms. Such substituents can also be further substituted.

The photographic elements can be single color elements or multicolor elements. Multicolor elements contain image dye-forming units sensitive to each of the three primary regions of the spectrum. Each unit can comprise a single emulsion layer or multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single segmented layer.

A typical multicolor photographic element comprises a support bearing a cyan dye image-forming unit comprised of at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler, and a yellow dye image-forming unit comprising at least one blue-sensitive silver halide emulsion layer having associated therewith at least one yellow dye-forming coupler. The element can contain additional layers, such as filter layers, interlayers, overcoat layers, subbing layers, and the like.

If desired, the photographic element can be used in conjunction with an applied magnetic layer as described in *Research Disclosure*, November 1992, Item 34390 published by Kenneth Mason Publications, Ltd., Dudley Annex, 12a North Street, Emsworth, Hampshire P010 7DQ, ENGLAND, the contents of which are incorporated herein by reference. When it is desired to employ the inventive materials in a small format film, *Research Disclosure*, June 1994, Item 36230, provides suitable embodiments.

In the following discussion of suitable materials for use in the emulsions and elements of this invention, reference will be made to *Research Disclosure*, September 1994, Item 36544, available as described above, which will be identified hereafter by the term "Research Disclosure". The contents of the Research Disclosure, including the patents and publications referenced therein, are incorporated herein by reference, and the Sections hereafter referred to are Sections of the Research Disclosure.

Except as provided, the silver halide emulsion containing elements employed in this invention can be either negative-working or positive-working as indicated by the type of processing instructions (i.e. color negative, reversal, or direct positive processing) provided with the element. Suitable emulsions and their preparation as well as methods of chemical and spectral sensitization are described in Sections I through V. Various additives such as UV dyes, brighteners, antifoggants, stabilizers, light absorbing and scattering materials, and physical property modifying addenda such as hardeners, coating aids, plasticizers, lubricants and matting agents are described, for example, in Sections II and VI through VIII. Color materials are described in Sections X through XIII. Scan facilitating is described in Section XIV. Supports, exposure, development systems, and processing methods and agents are described in Sections XV to XX. Certain desirable photographic elements and processing steps, particularly those useful in conjunction with color reflective prints, are described in *Research Disclosure*, Item 37038, February 1995.

Coupling-off groups are well known in the art. Such groups can determine the chemical equivalency of a coupler, i.e., whether it is a 2-equivalent or a 4-equivalent coupler, or modify the reactivity of the coupler. Such groups can advantageously affect the layer in which the coupler is coated, or other layers in the photographic recording material, by performing, after release from the coupler, functions such as dye formation, dye hue adjustment, development acceleration or inhibition, bleach acceleration or inhibition, electron transfer facilitation, color correction and the like.

The presence of hydrogen at the coupling site provides a 4-equivalent coupler, and the presence of another coupling-off group usually provides a 2-equivalent coupler. Representative classes of such coupling-off groups include, for example, chloro, alkoxy, aryloxy, hetero-oxy, sulfonyloxy, acyloxy, acyl, heterocyclyl, sulfonamido, mercaptotetrazole, benzothiazole, mercaptopropionic acid, phosphonyloxy, arylthio, and arylazo. These coupling-off groups are described in the art, for example, in U.S. Pat. Nos. 2,455,169, 3,227,551, 3,432,521, 3,476,563, 3,617,291, 3,880,661, 4,052,212 and 4,134,766; and in UK. Patents and published application Nos. 1,466,728, 1,531,927, 1,533,039, 2,006, 755A and 2,017,704A, the disclosures of which are incorporated herein by reference.

Image dye-forming couplers may be included in the element such as couplers that form cyan dyes upon reaction with oxidized color developing agents which are described in such representative patents and publications as: U.S. Pat. Nos. 2,367,531, 2,423,730, 2,474,293, 2,772,162, 2,895,826, 3,002,836, 3,034,892, 3,041,236, 4,333,999, 4,883,746 and "Farbkuppler-eine Literature Ubersicht," published in Agfa Mitteilungen, Band III, pp. 156–175 (1961). Preferably such couplers are phenols and naphthol that form cyan dyes on reaction with oxidized color developing agent.

Couplers that form magenta dyes upon reaction with oxidized color developing agent are described in such representative patents and publications as: U.S. Pat. Nos. 2,311,082, 2,343,703, 2,369,489, 2,600,788, 2,908,573, 3,062,653, 3,152,896, 3,519,429, and "Farbkuppler-eine Literature Ubersicht," published in Agfa Mitteilungen, Band III, pp. 126–156 (1961). Preferably such couplers are pyrazolones, pyrazolotriazoles, or pyrazolobenzimidazoles that form magenta dyes upon reaction with oxidized color developing agents.

Couplers that form yellow dyes upon reaction with oxidized color developing agent are described in such representative patents and publications as: U.S. Pat. Nos. 2,298,443, 2,407,210, 2,875,057, 3,048,194, 3,265,506, 3,447,928, 4,022,620, 4,443,536, and "Farbkuppler-eine Literature Ubersicht," published in Agfa Mitteilungen, Band III, pp. 112–126 (1961). Such couplers are typically open chain ketomethylene compounds.

Couplers that form colorless products upon reaction with oxidized color developing agent are described in such representative patents as: UK Patent No. 861,138; U.S. Pat. Nos. 3,632,345, 3,928,041, 3,958,993 and 3,961,959. Typically such couplers are cyclic carbonyl containing compounds that form colorless products on reaction with an oxidized color developing agent.

Couplers that form black dyes upon reaction with oxidized color developing agent are described in such representative patents as U.S. Pat. Nos. 1,939,231; 2,181,944; 2,333,106; and 4,126,461; German OLS No. 2,644,194 and German OLS No. 2,650,764. Typically, such couplers are resorcinols or m-aminophenols that form black or neutral products on reaction with oxidized color developing agent.

In addition to the foregoing, so-called "universal" or "washout" couplers may be employed. These couplers do not contribute to image dye-formation. Thus, for example, a naphthol having an unsubstituted carbamoyl or one substituted with a low molecular weight substituent at the 2- or 3-position may be employed. Couplers of this type are described, for example, in U.S. Pat. Nos. 5,026,628, 5,151,343, and 5,234,800.

It may be useful to use a combination of couplers any of which may contain known ballasts or coupling-off groups such as those described in U.S. Pat. No. 4,301,235; U.S. Pat. No. 4,853,319 and U.S. Pat. No. 4,351,897. The coupler may contain solubilizing groups such as described in U.S. Pat. No. 4,482,629. The coupler may also be used in association with "wrong" colored couplers (e.g. to adjust levels of interlayer correction) and, in color negative applications, with masking couplers such as those described in EP 213, 490; Japanese Published Application 58-172647; U.S. Pat. Nos. 2,983,608; 4,070,191; and 4,273,861; German Applications DE 2,706,117 and DE 2,643,965; UK Patent 1,530, 272; and Japanese Application 58-113935. The masking couplers may be shifted or blocked, if desired.

The invention materials may be used in association with materials that accelerate or otherwise modify the processing steps e.g. of bleaching or fixing to improve the quality of the image. Bleach accelerator releasing couplers such as those described in EP 193,389; EP 301,477; U.S. Pat. No. 4,163, 669; U.S. Pat. No. 4,865,956; and U.S. Pat. No. 4,923,784, may be useful. Also contemplated is use of the compositions in association with nucleating agents, development accelerators or their precursors (UK Patent 2,097,140; UK Patent 2,131,188); electron transfer agents (U.S. Pat. No. 4,859, 578; U.S. Pat. No. 4,912,025); antifogging and anti colormixing agents such as derivatives of hydroquinones, aminophenols, amines, gallic acid; catechol; ascorbic acid; hydrazides; sulfonamidophenols; and non color-forming couplers.

The invention materials may also be used in combination with filter dye layers comprising colloidal silver sol or yellow, cyan, and/or magenta filter dyes, either as oil-in-water dispersions, latex dispersions or as solid particle dispersions. Additionally, they may be used with "smearing" couplers (e.g. as described in U.S. Pat. No. 4,366,237; EP 96,570; U.S. Pat. No. 4,420,556; and U.S. Pat. No. 4,543, 323.) Also, the compositions may be blocked or coated in protected form as described, for example, in Japanese Application 61/258249 or U.S. Pat. No. 5,019,492.

The invention materials may further be used in combination with image-modifying compounds such as "Developer Inhibitor-Releasing" compounds (DIR's). DIR's useful in conjunction with the compositions of the invention are known in the art and examples are described in U.S. Pat. Nos. 3,137,578; 3,148,022; 3,148,062; 3,227,554; 3,384, 657; 3,379,529; 3,615,506; 3,617,291; 3,620,746; 3,701, 783; 3,733,201; 4,049,455 4,095,984; 4,126,459; 4,149,886; 4,150,228; 4,211,562 4,248,962; 4,259,437; 4,362,878; 4,409,323; 4,477,563 4,782,012; 4,962,018; 4,500,634; 4,579,816; 4,607,004 4,618,571; 4,678,739; 4,746,600; 4,746,601; 4,791,049 4,857,447; 4,865,959; 4,880,342; 4,886,736; 4,937,179 4,946,767; 4,948,716; 4,952,485; 4,956,269; 4,959,299 4,966,835; 4,985,336 as well as in patent publications GB 1,560,240; GB 2,007,662; GB 2,032, 914; GB 2,099,167; DE 2,842,063, DE 2,937,127; DE 3,636,824; DE 3,644,416 as well as the following European Patent Publications: 272,573; 335,319; 336,411; 346,899; 362,870; 365,252; 365,346; 373,382; 376,212; 377,463; 378,236; 384,670; 396,486; 401,612; 401,613.

Such compounds are also disclosed in "Developer-Inhibitor-Releasing (DIR) Couplers for Color Photography," C. R. Bart, J. R. Thirtle and P. W. Vittum in *Photographic Science and Engineering*, Vol. 13, p. 174 (1969), incorporated herein by reference. Generally, the developer inhibitor-releasing (DIR) couplers include a coupler moiety and an inhibitor coupling-off moiety (IN). The inhibitor-releasing couplers may be of the time-delayed type (DIAR couplers), which also include a timing moiety or chemical switch, which produces a delayed release of inhibitor. Examples of typical inhibitor moieties are: oxazoles, thiazoles, diazoles, triazoles, oxadiazoles, thiadiazoles, oxathiazoles, thiatriazoles, benzotriazoles, tetrazoles, benzimidazoles, indazoles, isoindazoles, mercaptotetrazoles, selenotetrazoles, mercaptobenzothiazoles, selenobenzothiazoles, mercaptobenzoxazoles, selenobenzoxazoles, mercaptobenzimidazoles, selenobenzimidazoles, benzodiazoles, mercaptooxazoles, mercaptothiadiazoles, mercaptothiazoles, mercaptotriazoles, mercaptooxadiazoles, mercaptodiazoles, mercaptooxathiazoles, telleurotetrazoles or benzisodiazoles. In a preferred embodiment, the inhibitor moiety or group is selected from the following formulas:

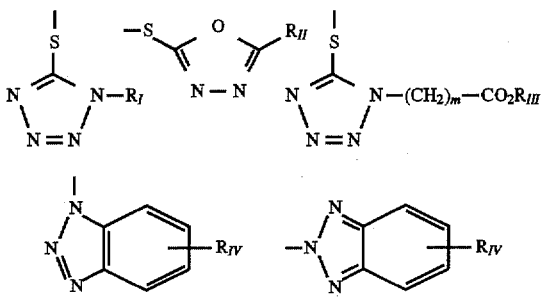

wherein $R_I$ is selected from the group consisting of straight and branched alkyls of from 1 to about 8 carbon atoms, benzyl, phenyl, and alkoxy groups and such groups containing none, one or more than one such substituent; $R_{II}$ is selected from $R_I$ and $-SR_I$; $R_{III}$ is a straight or branched alkyl group of from 1 to about 5 carbon atoms and m is from 1 to 3; and $R_{IV}$ is selected from the group consisting of hydrogen, halogens and alkoxy, phenyl and carbonamido groups, $-COOR_V$ and $-NHCOOR_V$ wherein $R_V$ is selected from substituted and unsubstituted alkyl and aryl groups.

Although it is typical that the coupler moiety included in the developer inhibitor-releasing coupler forms an image dye corresponding to the layer in which it is located, it may also form a different color as one associated with a different film layer. It may also be useful that the coupler moiety included in the developer inhibitor-releasing coupler forms colorless products and/or products that wash out of the photographic material during processing (so-called "universal" couplers).

As mentioned, the developer inhibitor-releasing coupler may include a timing group, which produces the time-delayed release of the inhibitor group such as groups utilizing the cleavage reaction of a hemiacetal (U.S. Pat. No. 4,146,396, Japanese Applications 60-249148; 60-249149); groups using an intramolecular nucleophilic substitution reaction (U.S. Pat. No. 4,248,962); groups utilizing an electron transfer reaction along a conjugated system (U.S. Pat. No. 4,409,323; 4,421,845; Japanese Applications 57-188035; 58-98728; 58-209736; 58-209738) groups utilizing ester hydrolysis (German Patent Application (OLS) No. 2,626,315); groups utilizing the cleavage of imino ketals (U.S. Pat. No. 4,546,073); groups that function as a coupler or reducing agent after the coupler reaction (U.S. Pat. No. 4,438,193; U.S. Pat. No. 4,618,571) and groups that combine the features describe above. It is typical that the timing group or moiety is of one of the formulas:

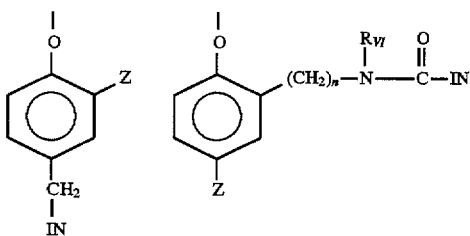

wherein IN is the inhibitor moiety, Z is selected from the group consisting of nitro, cyano, alkylsulfonyl; sulfamoyl (—$SO_2NR_2$); and sulfonamido (—$NRSO_2R$) groups; n is 0 or 1; and $R_{VI}$ is selected from the group consisting of substituted and unsubstituted alkyl and phenyl groups. The oxygen atom of each timing group is bonded to the coupling-off position of the respective coupler moiety of the DIAR.

Suitable developer inhibitor-releasing couplers for use in the present invention include, but are not limited to, the following:

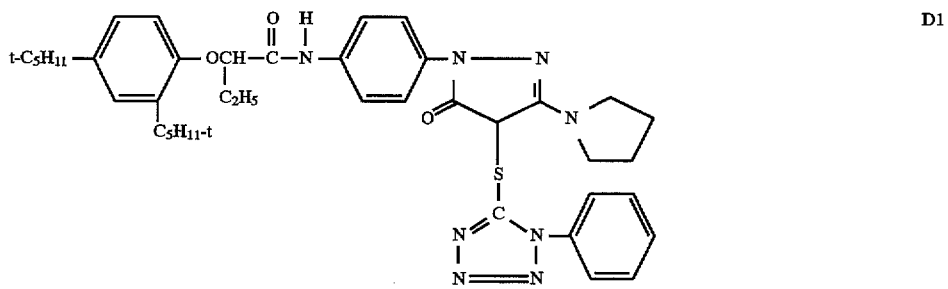

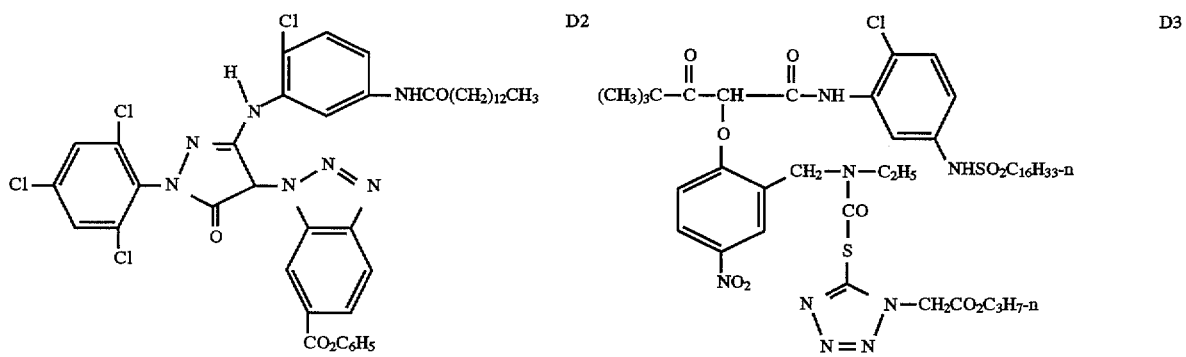

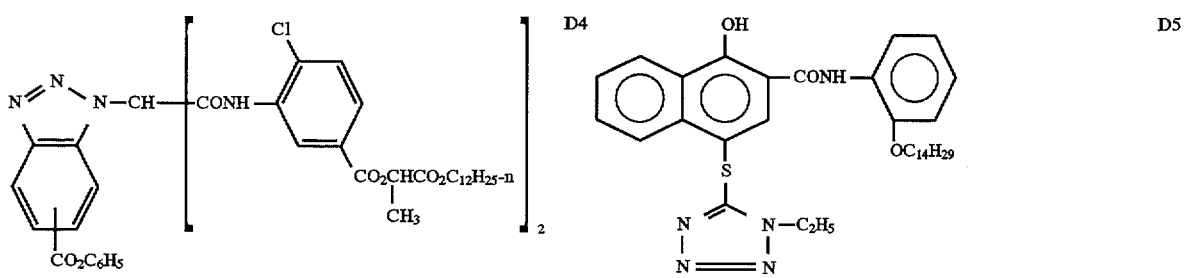

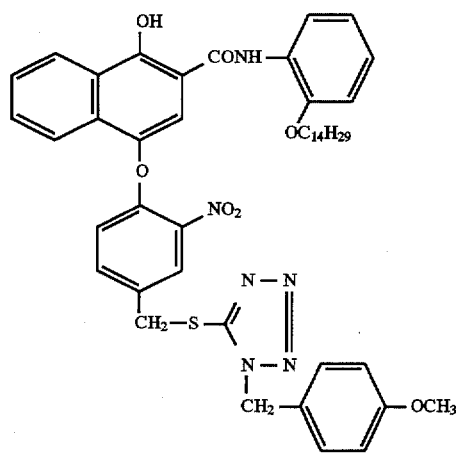

D6

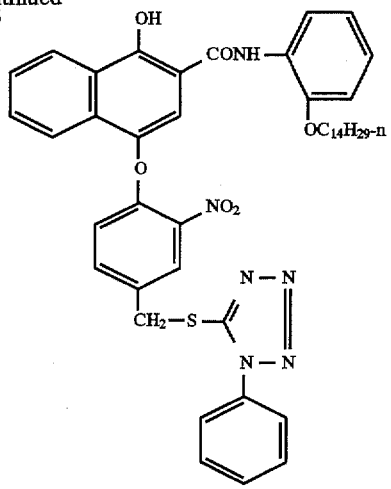

D7

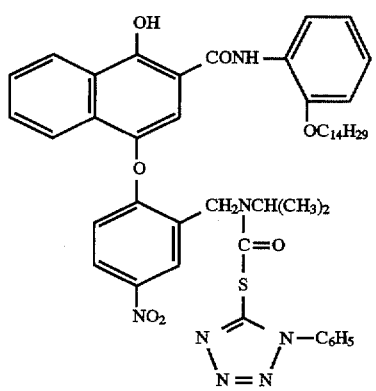

D8

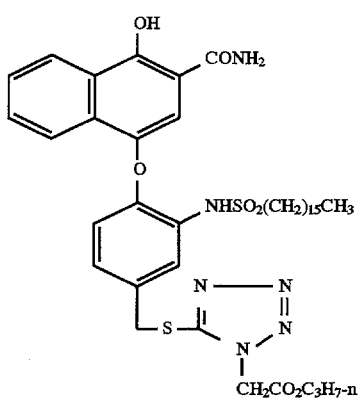

D9

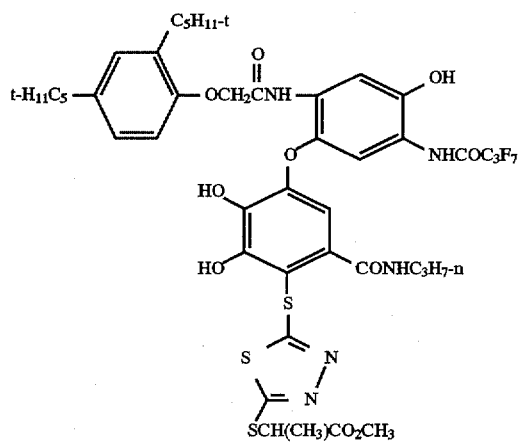

D10

It is also contemplated that the concepts of the present invention may be employed to obtain reflection color prints as described in Research Disclosure, November 1979, Item 18716, available from Kenneth Mason Publications, Ltd, Dudley Annex, 12a North Street, Emsworth, Hampshire P0101 7DQ, England, incorporated herein by reference. Materials of the invention may be coated on pH adjusted support as described in U.S. Pat. No. 4,917,994; on a support with reduced oxygen permeability (EP 553,339); with epoxy solvents (EP 164,961); with nickel complex stabilizers (U.S. Pat. No. 4,346,165; U.S. Pat. No. 4,540,653 and U.S. Pat. No. 4,906,559 for example); with ballasted chelating agents such as those in U.S. Pat. No. 4,994,359 to reduce sensitivity to polyvalent cations such as calcium; and with stain reducing compounds such as described in U.S. Pat. No. 5,068,171.

Other compounds useful in combination with the invention are disclosed in Japanese Published Applications described in Derwent Abstracts having accession numbers as follows: 90-072,629, 90-072,630; 90-072,631; 90-072,632; 90-072, 633; 90-072,634; 90-077,822; 90-078,229; 90-078,230; 90-079,336; 90-079,337; 90-079,338; 90-079,690; 90-079, 691; 90-080,487; 90-080,488; 90-080,489; 90-080,490; 90-080,491; 90-080,492; 90-080,494; 90-085,928; 90-086, 669; 90-086,670; 90-087,360; 90-087,361; 90-087,362; 90-087,363; 90-087,364; 90-088,097; 90-093,662; 90-093, 663; 90-093,664; 90-093,665; 90-093,666; 90-093,668; 90-094,055; 90-094,056; 90-103,409; 83-62,586; 83-09, 959.

Especially useful in this invention are tabular grain silver halide emulsions. Specifically contemplated tabular grain emulsions are those in which greater than 50 percent of the total projected area of the emulsion grains are accounted for by tabular grains having a thickness of less than 0.3 micron (0.5 micron for blue sensitive emulsion) and an average tabularity (T) of greater than 25 (preferably greater than 100), where the term "tabularity" is employed in its art recognized usage as $$T=ECD/t^2$$

where

ECD is the average equivalent circular diameter of the tabular grains in micrometers and t is the average thickness in micrometers of the tabular grains.

The average useful ECD of photographic emulsions can range up to about 10 micrometers, although in practice emulsion ECD's seldom exceed about 4 micrometers. Since both photographic speed and granularity increase with increasing ECD's, it is generally preferred to employ the smallest tabular grain CD's compatible with achieving aim speed requirements.

Emulsion tabularity increases markedly with reductions in tabular grain thickness. It is generally preferred that aim tabular grain projected areas be satisfied by thin (t<0.2 micrometer) tabular grains. To achieve the lowest levels of granularity it is preferred that aim tabular grain projected areas be satisfied with ultrathin (t<0.06 micrometer) tabular grains. Tabular grain thicknesses typically range down to about 0.02 micrometer. However, still lower tabular grain thicknesses are contemplated. For example, Daubendiek et al. U.S. Pat. No. 4,672,027 reports a 3 mole percent iodide tabular grain silver bromoiodide emulsion having a grain thickness of 0.017 micrometer. Ultrathin tabular grain high chloride emulsions are disclosed by Maskasky U.S. Pat. No. 5,217,858.

As noted above tabular grains of less than the specified thickness account for at least 50 percent of the total grain projected area of the emulsion. To maximize the advantages of high tabularity it is generally preferred that tabular grains satisfying the stated thickness criterion account for the highest conveniently attainable percentage of the total grain projected area of the emulsion. For example, in preferred emulsions, tabular grains satisfying the stated thickness criteria above account for at least 70 percent of the total grain projected area. In the highest performance tabular grain emulsions, tabular grains satisfying the thickness criteria above account for at least 90 percent of total grain projected area.

Suitable tabular grain emulsions can be selected from among a variety of conventional teachings, such as those of the following: Research Disclosure, Item 22534, January 1983, published by Kenneth Mason Publications, Ltd., Emsworth, Hampshire PO10 7DD, England; U.S. Patent Nos. 4,439,520; 4,414,310; 4,433,048; 4,643,966; 4,647,528; 4,665,012; 4,672,027; 4,678,745; 4,693,964; 4,713,320; 4,722,886; 4,755,456; 4,775,617; 4,797,354; 4,801,522; 4,806,461; 4,835,095; 4,853,322; 4,914,014; 4,962,015; 4,985,350; 5,061,069 and 5,061,616.

The emulsions can be surface-sensitive emulsions, i.e., emulsions that form latent images primarily on the surfaces of the silver halide grains, or the emulsions can form internal latent images predominantly in the interior of the silver halide grains. The emulsions can be negative-working emulsions, such as surface-sensitive emulsions or unfogged internal latent image-forming emulsions, or direct-positive emulsions of the unfogged, internal latent image-forming type, which are positive-working when development is conducted with uniform light exposure or in the presence of a nucleating agent.

Photographic elements can be exposed to actinic radiation, typically in the visible region of the spectrum, to form a latent image and can then be processed to form a visible dye image. Processing to form a visible dye image includes the step of contacting the element with a color developing agent to reduce developable silver halide and oxidize the color developing agent. Oxidized color developing agent in turn reacts with the coupler to yield a dye.

With negative-working silver halide, the processing step described above provides a negative image. The described elements can be processed in the known Kodak C-41 color process as described in The British Journal of Photography Annual of 1988, pages 191–198. Where applicable, the element may be processed in accordance with color print processes such as the RA-4 process of Eastman Kodak Company as described in the British Journal of Photography Annual of 1988, pp 198–199. Such negative working emulsions are typically sold with instructions to process using a color negative method such as the mentioned C-41 or RA-4 process. To provide a positive (or reversal) image, the color development step can be preceded by development with a non-chromogenic developing agent to develop exposed silver halide, but not form dye, and followed by uniformly fogging the element to render unexposed silver halide developable. Such reversal emulsions are typically sold with instructions to process using a color reversal process such as E-6. Alternatively, a direct positive emulsion can be employed to obtain a positive image.

Preferred color developing agents are p-phenylenediamines such as:

4-amino-N,N-diethylaniline hydrochloride, 4-amino-3-methyl-N,N-diethylaniline hydrochloride, 4-amino-3-methyl-N-ethyl-N-(2-methanesulfonamidoethyl) aniline sesquisulfate hydrate, 4-amino-3-methyl-N-ethyl-N-(2-hydroxyethyl)aniline sulfate, 4-amino-3-(2-methanesulfonamido-ethyl)-N,N-diethylaniline hydrochloride and 4-amino-N-ethyl-N-(2-methoxyethyl)-m-toluidine di-p-toluene sulfonic acid.

Development is usually followed by the conventional steps of bleaching, fixing, or bleach-fixing, to remove silver or silver halide, washing, and drying.

The entire contents of the various copending applications as well as patents and other publications cited in this specification are incorporated herein by reference.

Synthetic Example

Scheme 1 illustrates the synthesis of compound Mag-1, a representative coupler of this invention.

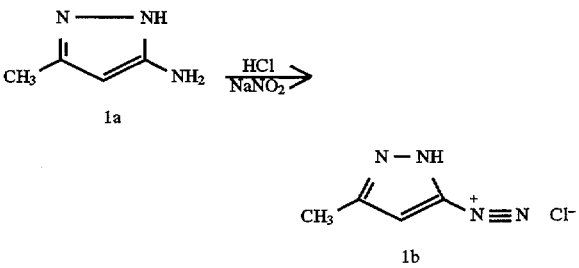

-continued
Scheme 1
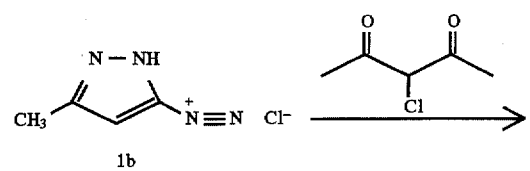
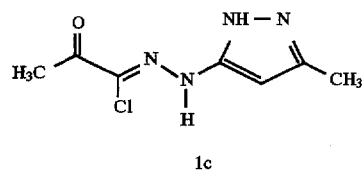
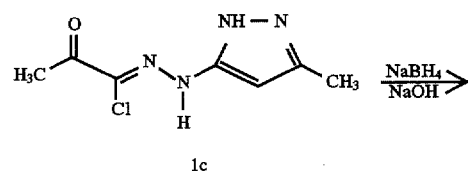
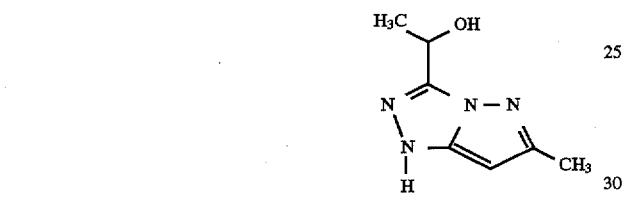
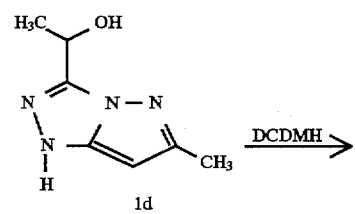
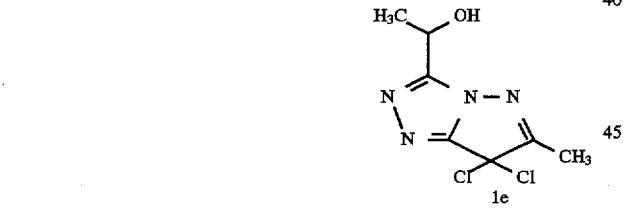
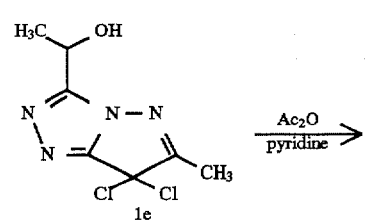
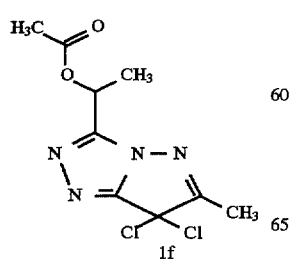
-continued
Scheme 1
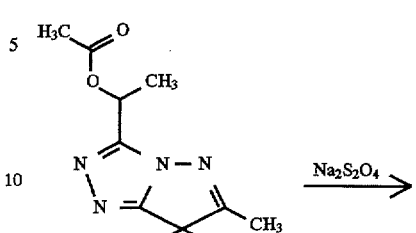 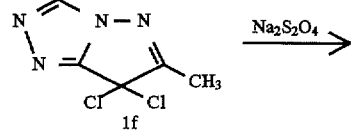
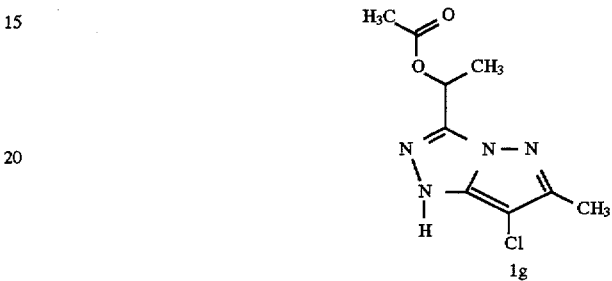
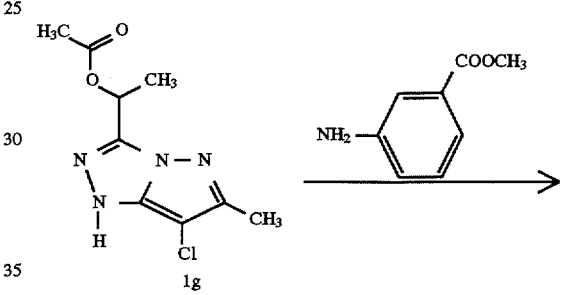
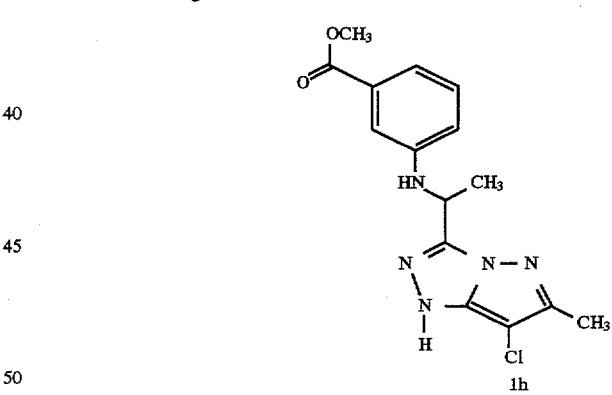
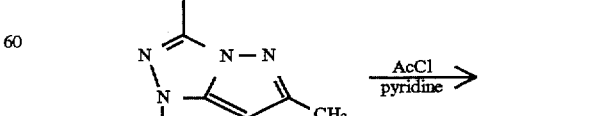
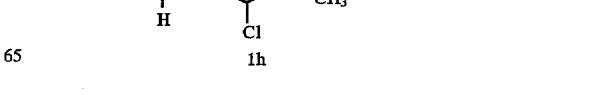

-continued
Scheme 1

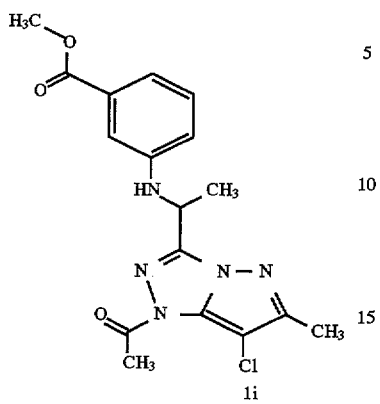

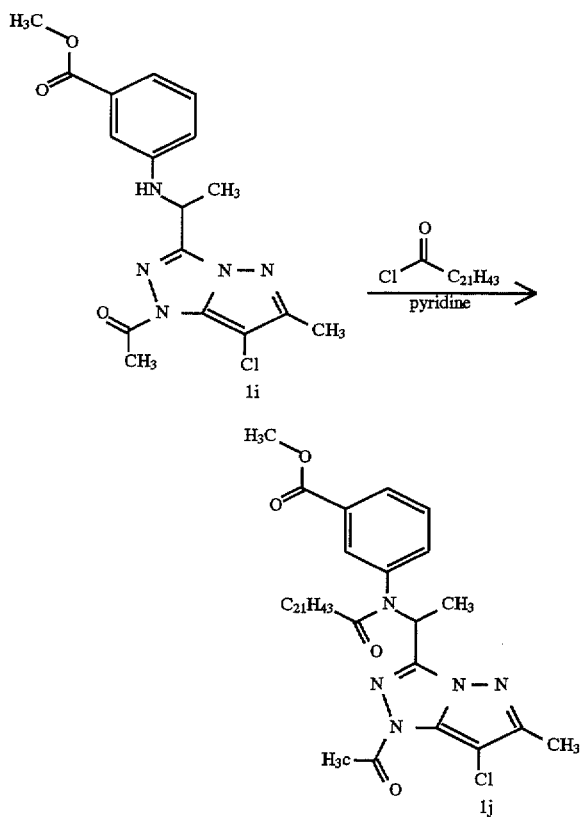

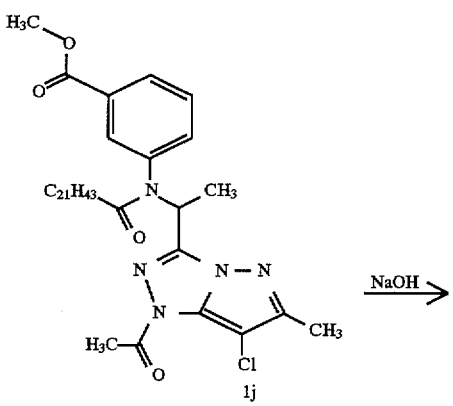

-continued
Scheme 1

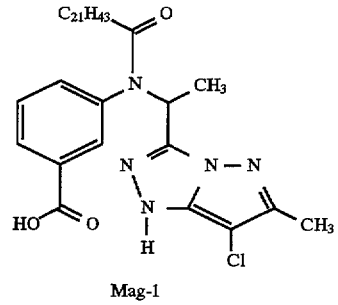

Diazotization of 5-amino-3-methyl-1H-pyrazole (1a) followed by Japp-Klingman reaction with an active methylene compound, 3-chloro-2,4-pentanedione, gives chlorohydrazone 1c, which is converted to the pyrazolotriazole 1d through reduction and ring closure reactions. Dichlorination of 1d with 1,3-dichloro-5,5-dimethylhydantoin (DCDMH) followed by acetylation and dechlorination gives 1g. This compound is then reacted in an elimination-addition reaction with methyl m-aminobenzoate to form 1b. Treatment with acetyl chloride to acylate the ring nitrogen yields 1i. Compound 1i is acylated with docosanoyl chloride, and the resulting product is treated with base to form Mag-1.

The following example illustrates the synthesis of a representative compound of this invention. All compounds were characterized by spectral methods including mass spec, NMR, IR and/or combustion analysis.

Synthesis of Example Mag-1

Steps 1 & 2: A solution of 10.9 g sodium nitrite in 30 mL water was slowly added to a solution of 19.2 g 5-amino-3-methylpyrazole (1a) in 25 mL 12M HCl and 40 mL water. The reaction temperature was maintained below 5° C. using an ice bath. After stirring for 30 min, the diazonium salt (1b) solution was added to a solution of 20 g of 3-chloro-2,4-pentanedione in 30 mL isopropyl alcohol, keeping the temperature at 15°–17° C. The reaction mixture was stirred at room temperature for 90 min and then a solution of 13 g sodium acetate in 40 mL water was added to the product slurry. The solids were collected, washed well with water, and dried to give 21 g (73% yield) of 1c. M/e=200, mp=165°–168° C., NMR and IR spectra were consistent with the reported structure.

Steps 3–6: A solution of 3.1 g sodium borohydride in 2 mL 0.1N NaOH was added dropwise to a solution of 3.3 g 1c in 45 mL isopropyl alcohol and 15 mL methanol, keeping the temperature below 35° C. The mixture was stirred for 1 h and then 4 g acetone was added to destroy any excess borohydride. The solution was neutralized with 12M HCl, treated with carbon and magnesium sulfate, and filtered. To the filtrate, containing 1d, was added 13 g 1,3-dichloro-5, 5-dimethylhydantoin (DCDMH), keeping the temperature under 40° C. The reaction mixture was stirred for 1 h and then added to 130 mL water and 100 mL dichloromethane with vigorous stirring. The two phases were separated, and the water layer was extracted twice with 100 mL each of dichloromethane. All dichloromethane extracts were combined, dried with magnesium sulfate, and filtered. The dichloromethane solution, containing intermediate 1e, was concentrated to half its original volume and 10.4 g pyridine, 0.3 g 4-N,N-dimethylaminopyridine (DMAP), and 26 g acetic anhydride were added, while keeping the temperature below 30° C. The reaction mixture was stirred for 1 h and a solution of 13 g sodium dithionite in 70 mL water was added. The two phase reaction mixture was well stirred for 1 h, then the phases were allowed to separate and the water layer was discarded. The organic layer was washed with 1M HCl and water, dried over magnesium sulfate, and filtered. The solution was concentrated to an oil under reduced pressure. The oil was crystallized from 20 mL toluene and 20 mL heptane. The solids were filtered, washed with cyclohexane, and dried to give 5.5 g (34% overall yield from 1c) of 1g. M/e=242, mp=110°–112° C., NMR and IR spectra were consistent with the reported structure.

Steps 7: To a stirred solution of 1g (7.3 g, 30.0 mmol) in THF (109 mL) was added methyl m-aminobenzoate (4.6 g, 30.0 mmol) and triethylamine (3.1 g, 30.0 mmol). The mixture was heated to 45° C. for 6 h. The mixture was cooled to room temperature, diluted with EtOAc (350 mL) and washed 2×350 mL with 5% HCl followed by 2×350 mL with brine. The organic layer was then dried over $MgSO_4$ and concentrated under reduced pressure. The resulting solid was purified by trituration with toluene to yield 7.4 g (74%) of 1h. M/e=332, mp=166°–168° C., H NMR was consistent with the reported structure.

Step 8: To a stirred mixture of 1h (11.6 g, 34.8 mmol) in EtOAc (150 mL) at 0° C. was added pyridine (3.35 mL, 41.7 mmol). A solution of acetyl chloride (3.0 mL, 41.7 mmol) in EtOAc (15 mL) was added dropwise. When the addition was complete, the reaction mixture was allowed to warm to room temperature and stir for 1 h. The mixture was then diluted with EtOAc (200 mL) and washed with 5% HCl followed by brine. The organic layer was then dried over $MgSO_4$ and concentrated under reduced pressure. The resulting oil was purified by column chromatography on silica with a solvent gradient of heptane and EtOAc to afford 13 g (99%) of a 1i as a white solid. mp=120°–122° C., NMR spectra were consistent with the reported structure.

Step 9: To a stirred mixture of 1i (7.85 g, 20.9 mmol) in toluene (80 mL) was added docosanoyl chloride (7.5 g, 20.9 mmol). The reaction mixture was heated to reflux for 7 h. The reaction mixture was then concentrated under reduced pressure and dissolve in $CH_2Cl_2$ and added to the top of a pad of silica. The product was eluted with EtOAc:heptane 1:4. The resulting oil was crystallized from hot $CH_3CN$ to yield 9.2 g (62%) of 1j as a white solid. Mp=74°–75° C.

Step 10: A stirred solution of 1j (5.0 g, 7.2 mmol) in THF (20 mL) was diluted with MeOH (10 mL) and then treated with a solution of sodium hydroxide (1.1 g, 29 mmol) in water (10 mL). The reaction mixture was allowed to stir at room temperature for 1 h, and then was quenched by adding 5% HCl (100 mL). The mixture was extracted with EtOAc (100 mL). The organic layer was washed with brine, dried over $MgSO_4$, and concentrated under reduced pressure. The resulting foam was crystallize from EtOAc/$CH_3CN$ (1:1) to yield 4.4 g (96%) of Mag-1 as a white solid. $MH^+$=642, mp=139°–142° C., NMR spectra were consistent with the reported structure.

Photographic Examples

To measure the pH sensitivity of a single layer film, the following was done. A stepped exposure was applied to three identical strips of the film. One strip was processed with the normal C-41 process at pH of about 10. A second strip was processed in the same developer in which the pH was decreased to 9.75, while the third strip was processed in the same developer in which the pH was increased to 10.37.

Single layer films demonstrating the principles of this invention were produced by coating the magenta couplers, with the presence of DIR-3, together with an emulsion on a cellulose acetate support. The emulsion was an undyed, but chemically sensitized, 0.7 micron polymorphic silver iodobromide emulsion containing 3.5% mole of iodide. The coating structure is shown below.

Monolayer coatings were panchromatically exposed and processed in developer solutions of different pH values. A stop bath was used to eliminate any complications due to the continuing coupling reaction. The processing procedure and solution formulations are listed below.

| Single Layer Format | | |
|---|---|---|
| Overcoat | Gelatin | 2690 mg/m² |
| | Bis(vinylsulfonylmethyl) ether | 129 mg/m² |
| Monolayer | Gelatin | 3766 mg/m² |
| | Emulsion | 904 mg/m² |
| | Coupler Dispersion | 1.08 mmol/m² |
| | DIR Dispersion | 75 mg/m² |

Cellulose Acetate Support

| Development Process | |
|---|---|
| C-41 DEV (different pH) | 2' |
| Stop Bath | 30" |
| Wash | 2' |
| Flexicolor II Bleach | 3' |
| Wash | 3' |
| C-41 Fix Repl. | 4' |
| Wash | 3' |
| Photoflo | 301" |
| Process run at 100° F. | |

| Processing Solution Formulations | |
|---|---|
| 1. C-41 Developer (pH 10) | |
| Water | 800.0 mL |
| Potassium carbonate, anhydrous | 34.30 g |
| Potassium bicarbonate | 2.32 g |
| Sodium sulfite, anhydrous | 0.38 g |
| Sodium metabisulfite | 2.78 g |
| Potassium iodide | 1.20 mg |
| Sodium bromide | 1.31 g |
| Diethylenetriaminepentaacetic acid pentasodium salt (40% solution) (KODAK Anti-Calcium No. 8) | 8.43 g |
| Hydroxylamine sulfate (HAS) | 2.41 g |
| KODAK Color Developing Agent CD-4 | 4.52 g |
| Water to make | 1.00 L |
| pH at 80° F. 10.00 +/− 0.05 | |
| 2. Developer solution of pH 9.75: Obtained by adjusting the developer solution of pH 10 with sulfuric acid. | |
| 3. Developer solution of pH 10.37: Obtained by adjusting the developer solution of pH 10 with sodium hydroxide. | |

| Kodak Flexicolor Bleach II | |
|---|---|
| Water | 600.0 mL |
| Ammonium bromide | 50.00 g |
| 1,3-Propanediaminetetraacetic acid (PDTA) | 30.27 g |
| Ammonium hydroxide (28% ammonia) | 35.20 g |
| Ferric nitrate nonahydrate | 36.40 g |
| Glacial acetic acid | 26.50 g |
| 1,3-Diamino-2-propanoltetraacetic acid (Rexpronol Acid, Grace) | 1.00 g |
| Ammonium ferric EDTA (1.56 M, pH 7.05, 44% wt.) (contains 10% molar excess EDTA, 3.5% wt.) (KODAK Solution No. 3422) | 149.00 g |
| Water to make | 1.00 L |
| pH at 80° F. 5.25 +/− 0.10 adjust pH with $NH_4OH$ or $HNO_3$ | |

| Kodak Flexicolor Fix | |
|---|---|
| Water | 500.0 mL |
| Ammonium thiosulfate (58%) | 214.00 g |

| | |
|---|---|
| solution) (less than 1% ammonium sulfite) | |
| (Ethylenedinitrilo)tetraacetic acid disodium salt, dehydrate | 1.29 g |
| Sodium metabisulfite | 11.00 g |
| Sodium hydroxide (50% solution) | 4.70 g |
| Water to make | 1.00 L |
| pH at 80° F. 6.50 +/- 0.15 | |

The D-logE Status M gamma was measured for each film and the three gammas were used as input to a least-squares regression in which gamma was the response, and the factors were pH and pH-squared in a linear model with an intercept. Before regression, the three pH values were shifted (centered) to have a mean of zero (-0.31, 0, 0.31). The coefficient of the main effect, pH, in the regression is the pH sensitivity of gamma, which was normalized by division with the pH sensitivity of the comparison coupler C-1 (Table 2) that was processed at the same time as each test coupler.

Further single layer film elements were prepared as above, given a stepped exposure and processed (developer pH=10). The activity of an image coupler was determined by determining the maximum slope between any two adjacent steps for the coupler and dividing by the maximum slope of a corresponding control sample containing coupler C-1 processed at the same time as the sample. A higher ratio implies higher activity. The logP of the $R_3$ fragment (a quantity also referred to as $\pi$) was calculated as described in the Detailed Description of the invention. Comparison couplers are shown in Table 2. Results are shown in Table 3.

TABLE 2

Comparison Couplers

| Example | Structure |
|---|---|
| C-1 | 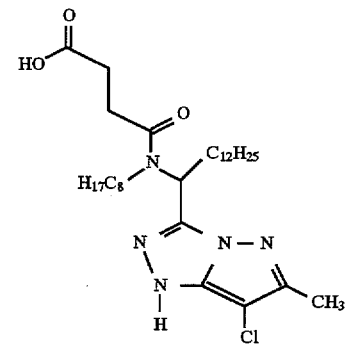 |
| C-2 | 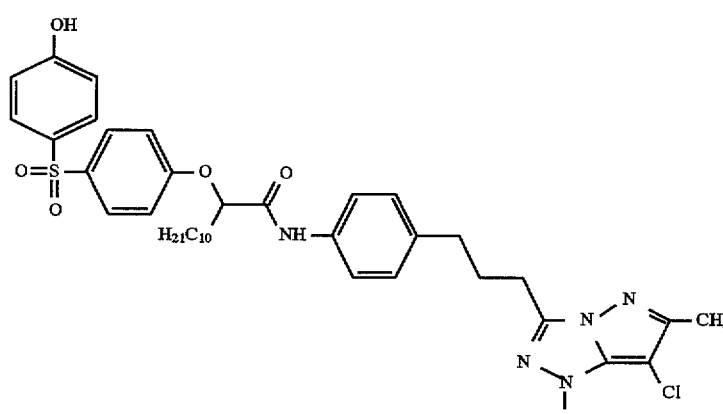 |
| C-4 | 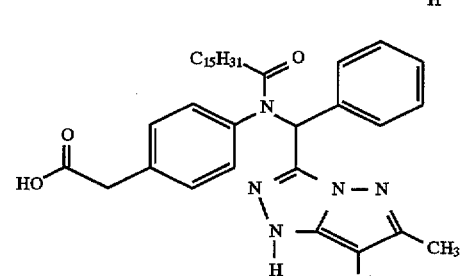 |

TABLE 2-continued

Comparison Couplers

| Example | Structure |
|---|---|
| C-5 | (structure: 4-carboxybenzyl group attached to N bearing C₁₅H₃₁C(=O)— and a CH(CH₃)— linked to a C(=N-NH-)— pyrazole ring with Cl and CH₃ substituents) |
| C-7 | (structure: HOOC-(CH₂)₅-N with C₁₇H₃₅C(=O)— and CH(CH₃)— linked to pyrazole ring with Cl and CH₃) |
| C-8 | (structure: 3-(carboxymethyl)phenyl-N(C₁₅H₃₁C(=O))-CH(C₆H₅)- linked to pyrazole ring with Cl and CH₃) |
| C-9 | (structure: complex pyrazolone coupler with C₁₃H₂₇C(=O)NH- aniline, 2,4,6-trichlorophenylazo group, and thioether linked to 2,4-di-t-amylphenoxy ethyl amide) |

TABLE 2-continued

Comparison Couplers

| Example | Structure |
|---------|-----------|
| C-10 | 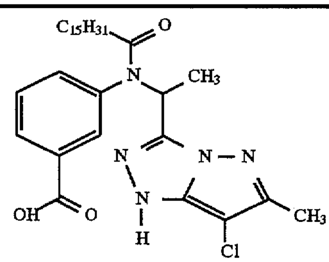 |
| C-11 | 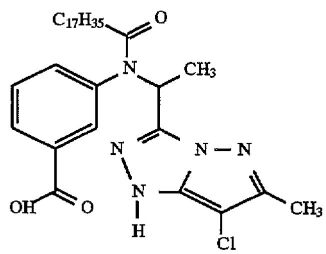 |
| C-12 | 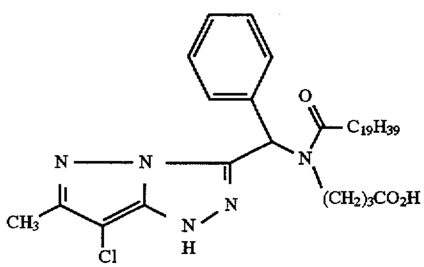 |
| C-13 | 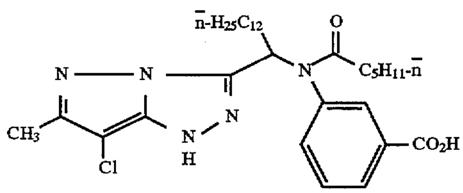 |
| C-14 | 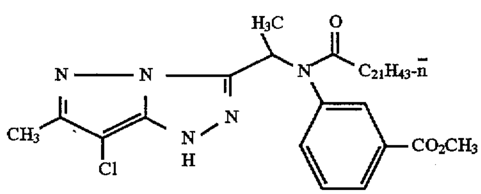 |
| C-15 | 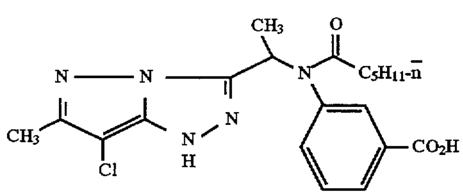 |

TABLE 3

Activity and pH Sensitivity in Single Layer Format

| Experiment | Comp/Inv | Coupler | Activity | Calculated LogP of $R_3$ | pH Sensitivity |
|---|---|---|---|---|---|
| SL-1 | Comp | C-1 | 1.00 | −0.43 | 1.00 |
| SL-2 | Comp | C-2 | 0.51 | — | 1.39 |
| SL-3 | Comp | C-4 | 0.87 | 7.91 | 1.32 |
| SL-4 | Comp | C-5 | 1.34 | 7.91 | 1.32 |
| SL-5 | Comp | C-7 | 1.04 | 8.97 | 1.32 |
| SL-6 | Comp | C-8 | 1.26 | 7.91 | 1.43 |
| SL-7 | Comp | C-12 | 0.91 | — | 0.75 |
| SL-8 | Comp | C-13 | 1.33 | 2.62 | |
| SL-9 | Comp | C-10 | 1.52 | 7.91 | 0.51 |
| SL-10 | Comp | C-11 | 1.33 | 8.97 | 1.05 |
| SL-11 | Comp | C-14 | 0.43 | 11.08 | |
| SL-12 | Inv | Mag-1 | 1.50 | 11.08 | 0.83 |
| SL-13 | Inv | Mag-6 | 1.15 | 11.50 | 0.75 |
| SL-14 | Inv | Mag-7 | 1.22 | 11.49 | 0.83 |

The pH sensitivity values shown in Table 3 confirm that the pH sensitivity of a photographic element of the invention is far less developer pH dependent than are comparable elements of the art. For the invention, the pH sensitivities range from 0.75 to 0.83. On the other hand the values for the comparative single layer elements where the coupler had an $R_3$ logP of 9 or less were well over 1.0. Thus the element of the invention is desirably less developer pH sensitive.

It is further observed that the activity of the inventive couplers is generally superior to the comparisons. In particular, SL-11 shows substantial loss of activity resulting from the use of the methyl ester as opposed to the carboxylic acid of Mag-1.

Multilayer films demonstrating the principles of this invention were produced by coating the following layers on a cellulose triacetate film support (coverage are in grams per meter squared, emulsion sizes as determined by the disc centrifuge method and are reported in Diameter×Thickness in microns). The formulas for the multilayer organic components are provided following the examples. The multilayer format used was an ISO 200 speed format (designated ML-A).

Format ML-A

Layer 1 (Antihalation layer): black colloidal silver sol at 0.140; gelatin at 2.15; OxDS-1 at 0.108; DYE-1 at 0.049, DYE-2 at 0.017, DYE-3 at 0.014, DYE-4 at 0.065 and DYE-5 at 0.075.

Layer 2 (Slow cyan layer): a blend of three red sensitized (all with a mixture of RSD-1 and RSD-2) silver iodobromide emulsions: (i) a large sized tabular grain emulsion (1.3×0.118, 4.1 mole % I) at 0.522 (ii) a smaller tabular emulsion (0.85×0.115, 4.1 mole % I) at 0.337 and (iii) a very small tabular grain emulsion (0.55×0.115, 1.5 mole % I) at 0.559; gelatin at 2.85; cyan dye-forming coupler CC-1 at 0.452; DIR coupler DIR-1 at 0.043; bleach accelerator releasing coupler B-1 at 0.054 and anti-foggant 4-hydroxy-6-methyl-1,3,3a,7-tetraazaindene at 0.016.

Layer 3 (Fast cyan layer): a red-sensitized (same as above) tabular silver iodobromide emulsion (2.2×0.128, 4.1 mole % I) at 0.086; cyan coupler CC-1 at 0.081; DIR-1 at 0.034; MC-1 at 0.043; gelatin at 1.72 and anti-foggant 4-hydroxy-6-methyl-1,3,3a,7-tetraazaindene at 0.010.

Layer 4 (Interlayer): gelatin at 1.29.

Layer 5 (Slow magenta layer): a blend of two green sensitized (both with a mixture of GSD-1 and GSD-2) silver iodobromide emulsions: (i) 0.54×0.091, 4.1 mole % iodide at 0.194 and (ii) 0.52×0.085, 1.5 mole % iodide at 0.559; magenta dye forming coupler at the indicated laydown; gelatin at 1.08 and anti-foggant 4-hydroxy-6-methyl-1,3,3a,7-tetraazaindene at 0.005.

Layer 6 (Mid magenta layer): a blend of two green sensitized (same as above) tabular silver iodobromide emulsions (i) 1.3×0.113, 4.1 mole % I at 0.430 and (ii) 0.54×0.91, 4.1 mole % I at 0.172; magenta dye forming coupler at the indicated laydown; MC-2 at 0.015; DIR-2 at 0.016; gelatin at 2.12 and anti-foggant 4-hydroxy-6-methyl-1,3,3a,7-tetraazaindene at 0.003.

Layer 7 (Fast magenta layer): a green sensitized tabular silver iodobromide (1.8×0.127, 4.1 mole % I) emulsion at 0.689; gelatin at 1.61; magenta dye forming coupler at the indicated laydown; MC-2 at 0.054 and DIR-3 at 0.003.

Layer 8 (Yellow filter layer): gelatin at 0.86; Carey-Lea silver at 0.043 and OxDS-2 at 0.054.

Layer 9 (Slow yellow layer): an equal blend of three blue sensitized (both with BSD-1) tabular silver iodobromide emulsions (i) 0.50×0.085, 1.5 mole % I (ii) 0.60 diameter, 3% mole I and (iii) 0.68 diameter, 3 mole % I at a total of 0.430; yellow dye forming coupler Y-1 at 0.699; yellow dye forming coupler Y-2 at 0.215; DIR-4 at 0.086; C-1 at 0.097 and gelatin at 2.066.

Layer 10 (Fast yellow layer): two blue sensitized (with BSD-1) tabular silver iodobromide emulsions (i) 3.1×137, 4.1 mole % I at 0.396 (ii) 0.95 diameter, 7.1 mole % I at 0.47; F at 0.131; B at 0.215; DIR-4 at 0.075; C-1 at 0.011; B-1 at 0.008 and gelatin at 1.08.

Layer 11 (Protective overcoat and UV filter layer): gelatin at 1.61; silver bromide Lippman emulsion at 0.215; DYE-4 and DYE-5 (1:1 ratio) at a total of 0.023 and bis (vinylsulfonyl)methane hardener at 1.6% of total gelatin weight.

Surfactants, coating aids, emulsion addenda, sequestrants, lubricants, matte and tinting dyes were added to the appropriate layers as is common in the art.

Table 4 indicates the experiment number, whether it is a comparative or inventive example, the magenta coupler used in the designated green sensitive layers and the laydown in each of those layers.

TABLE 4

Magenta Coupler and Laydowns (in $g/m^2$) in Multilayer Format

| Experiment | Comp/Inv | Magenta | Layer 5 | Layer 6 | Layer 7 |
|---|---|---|---|---|---|
| ML-1 | Comp | C-1 | 0.237 | 0.070 | 0.036 |
| ML-2 | Comp | C-15 | 0.189 | 0.048 | 0.027 |
| ML-3 | Comp | C-10 | 0.253 | 0.065 | 0.036 |
| ML-4 | Comp | C-11 | 0.266 | 0.068 | 0.037 |
| ML-5 | Inv | Mag-1 | 0.291 | 0.074 | 0.042 |
| ML-6 | Inv | Mag-11 | 0.222 | 0.055 | 0.032 |
| ML-7 | Inv | Mag-7 | 0.327 | 0.084 | 0.046 |

To measure the green pH sensitivity of a multilayer film, the following was done. A neutral stepped exposure was applied to nine 35-mm strips of the film. One strip was processed with the normal C-41 process. The other eight strips were processed in a 2**3 factorial design in which the pH of the developer solution was varied from 9.95 to 10.15, the bromide was varied from 0.8 g/L to 1.8 g/L, and the concentration of the developer was varied from 3.5 g/L to 5.5 g/L. The green Status M photographic D-logE gammas were measured for each film at mid-exposure, and each gamma was normalized by dividing by the average gamma for all nine strips.

The nine normalized gammas that were obtained at the nine combinations of pH, Br, and developer concentration were used as input to a least-squares regression in which normalized gamma was the response, and the factors were pH, Br, and developer concentration in a linear model with an intercept. The coefficient of pH is the sensitivity of normalized gamma to pH, and this was further normalized (divided) by the sensitivity of the comparison coupler C-1 (Table 2) that was processed at the same time as each test coupler. These relative normalized pH sensitivities of gamma are shown in Table 5.

Coupler wandering (solution of the coupler at the high pH of the developer and diffusion into another imaging layer) was determined by giving the multilayer coatings a stepped exposure of the blue and red layers only (no exposure of the green layer) and processing using standard C-41 conditions at pH 10 as previously described in the application. These coatings were then cross-sectioned and examined by optical microscope. Since there was no green exposure, no magenta dye should be formed (except for fog). If the magenta coupler wanders, then magenta dye will be visible in the yellow (blue light sensitive) or cyan (red light sensitive) layers. Table 5 contains the wandering test results as well as the normalized green pH sensitivities of gamma (calculated as described above). It was noted that very little magenta dye formed from coupler C-15 remained in the film after processing due to the solubility of its magenta dye and subsequent washout from the film; thus its pH sensitivity results may not be directly comparable to the other couplers since the resulting green gamma is not derived from C-15 but rather the other magenta dye forming components of the system.

TABLE 5 pH Sensitivity and Coupler Wandering of Magenta Couplers in Multilayer

| Experiment | Comp/Inv | Magenta | logP | pH Sensitivity | Wandering |
|---|---|---|---|---|---|
| ML-1 | Comp | C-1 | −0.4 | 1.00 | No |
| ML-2 | Comp | C-15 | 2.67 | 0.41 | Yes |
| ML-3 | Comp | C-10 | 7.9 | 0.66 | Yes |
| ML-4 | Comp | C-11 | 8.97 | 0.63 | Yes |
| ML-5 | Inv | Mag-1 | 11.08 | 0.52 | No |
| ML-6 | Inv | Mag-11 | 11.50 | 0.56 | No |
| ML-7 | Inv | Mag-7 | 11.49 | 0.59 | No |

It is observed that the undesirable wandering is avoided when the logP is greater that 9.0.

It can be clearly seen from the single layer and multilayer experiments that only the inventive couplers fully satisfy the need for high efficiency with low sensitivity to pH variations without color contamination due to coupler wandering.

Formulas for the multilayers were as follows:

Dye-1:

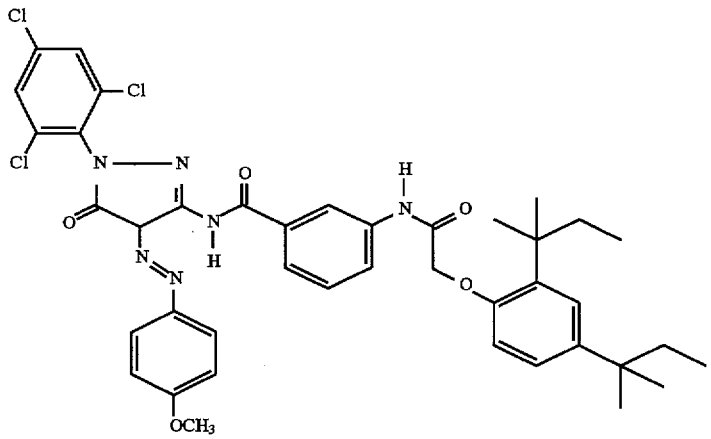

Dye-2:

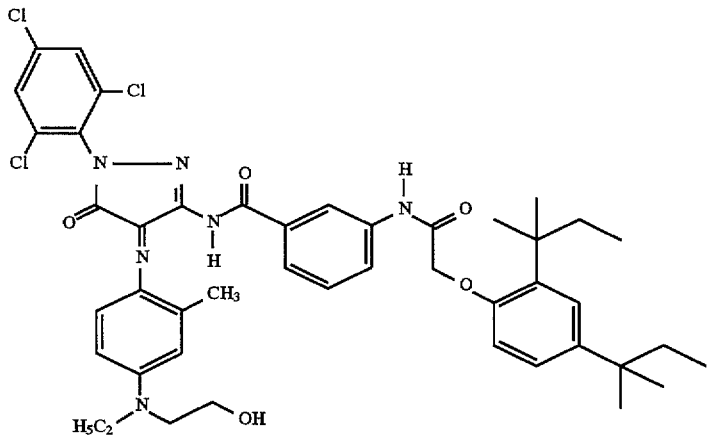

Dye-3:
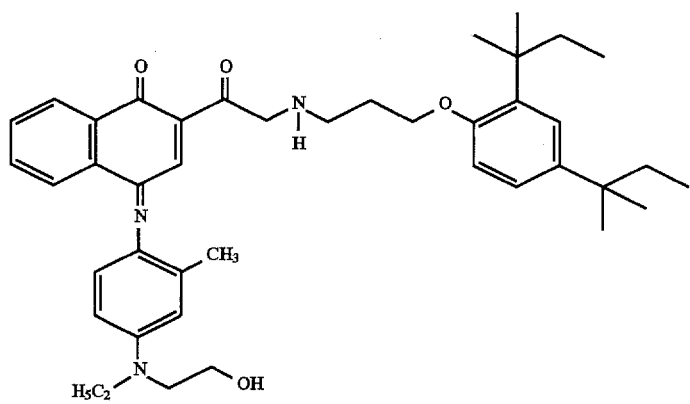
Dye-4:
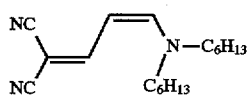
Dye-5:
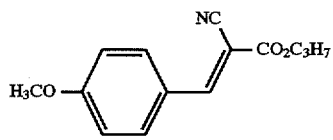
Dye-6:
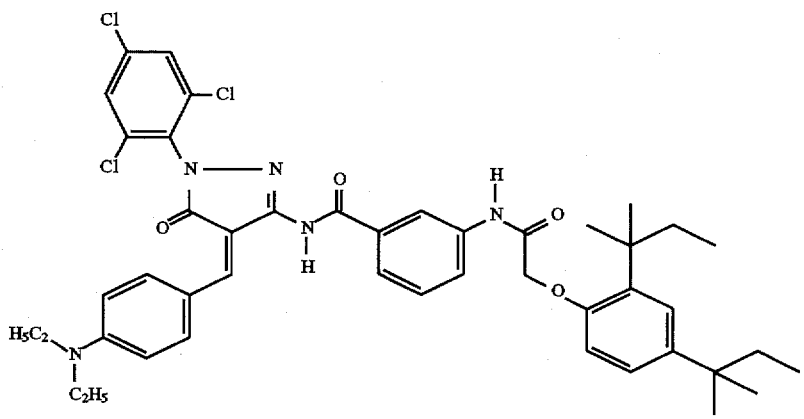
Dye-7:
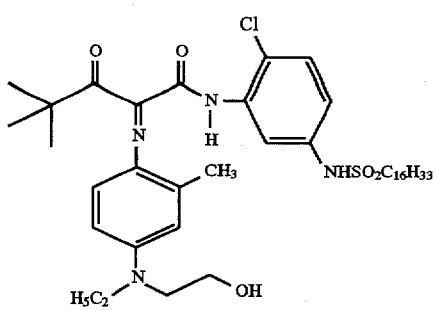

OxDS-1:
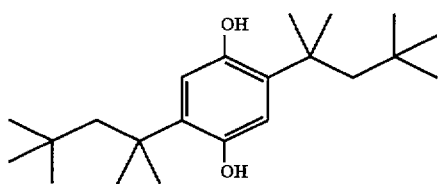
OxDS-2:
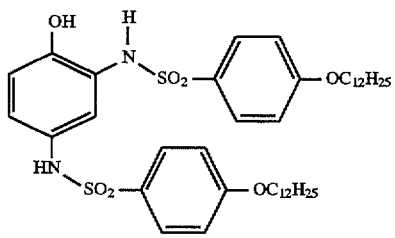
CC-1:
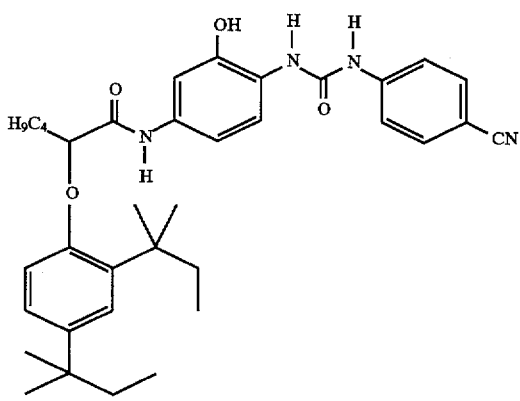
Y-1:
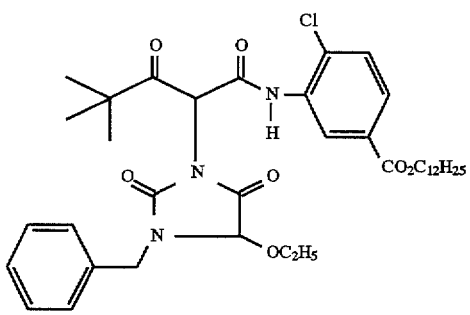
Y-2:
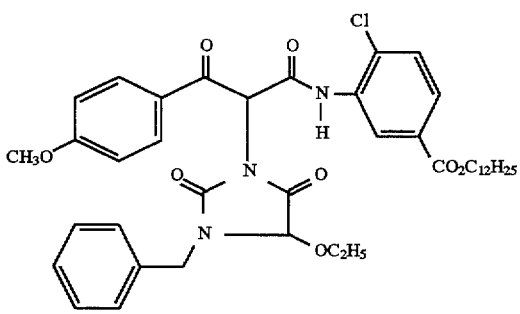

B-1:
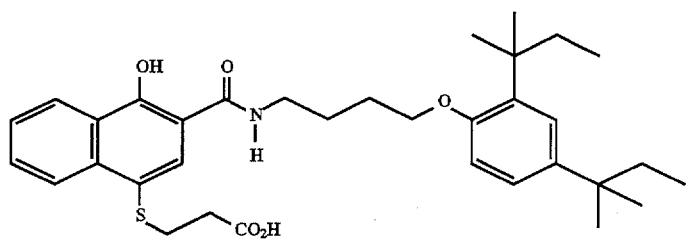
MC-1:
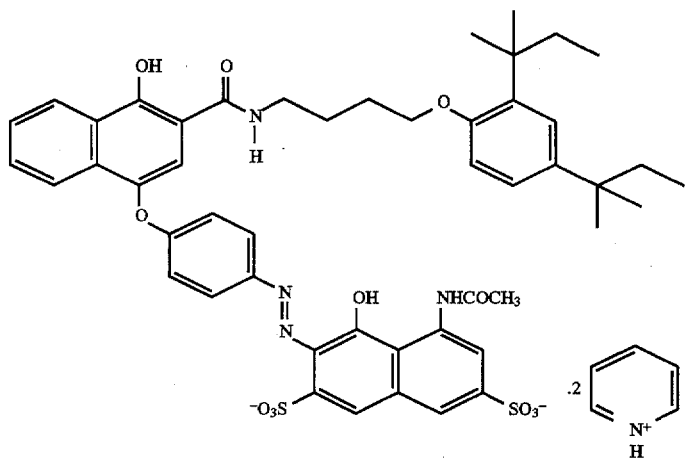
MC-2:
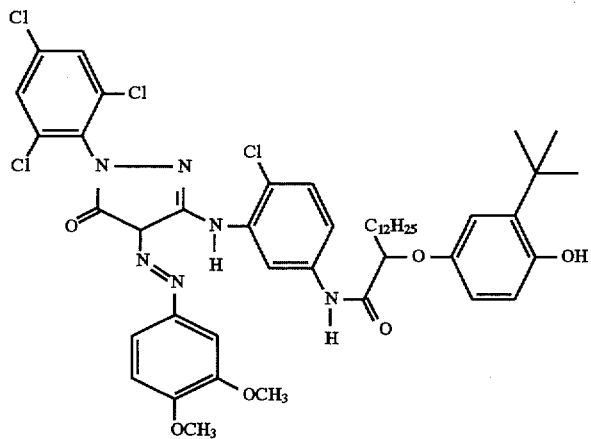

DIR-1:
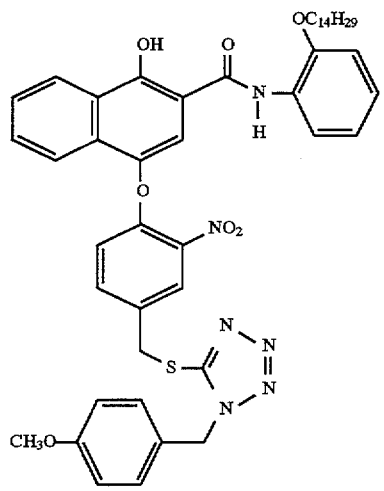
DIR-2:
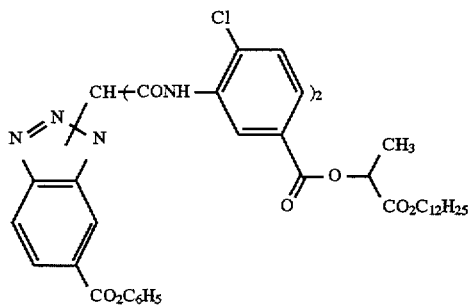
DIR-3:
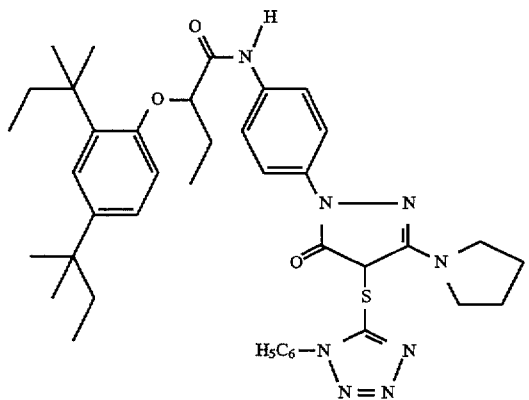

DIR-4:
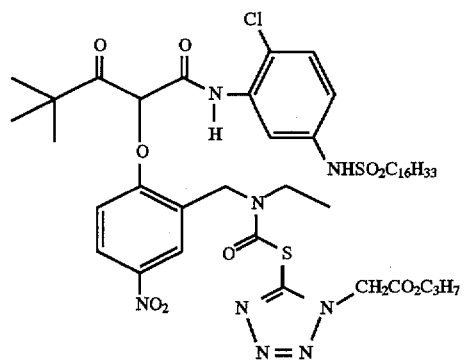
DIR-5:
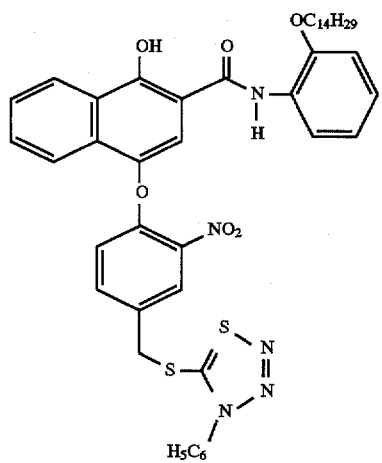
DIR-6:
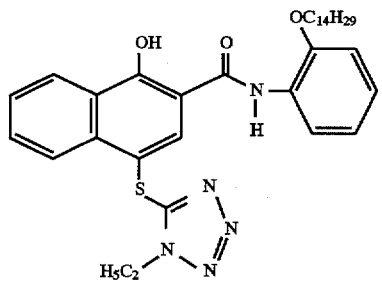
YFD-1:
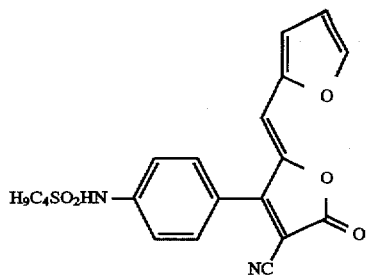

RSD-1:
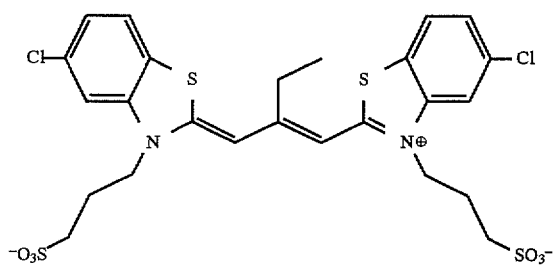
RSD-2:
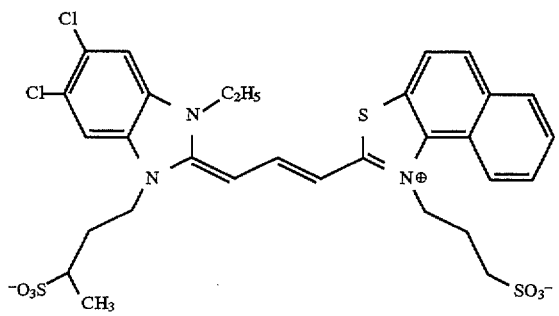
GSD-1:
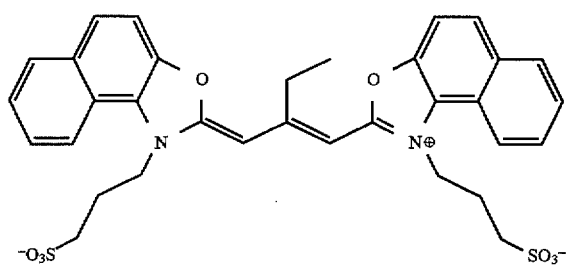
GSD-2:
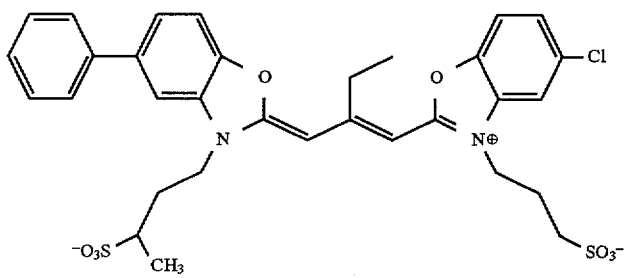
BSD-1:
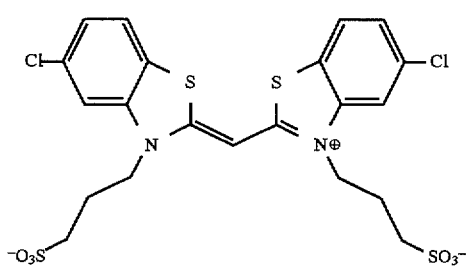

What is claimed is:

1. A photographic element comprising a light sensitive silver halide emulsion layer having associated therewith a dye-forming coupler having formula I:

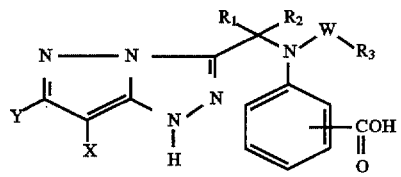

wherein
- $R_1$ is selected from the group consisting of alkyl, aryl, and heterocyclic groups;
- $R_2$ is selected from the group consisting of hydrogen, alkyl, aryl, and heterocyclic groups;
- W is C(O) or S(O)$_2$;
- $R_3$ is selected from the group consisting of alkyl and aryl groups having a calculated logP of at least 9;
- Y is a substituent; and
- X is H or a coupling-off group.

2. The element of claim 1 wherein W is C(O).
3. The element of claim 1 wherein W is S(O)$_2$.
4. The element of claim 1 wherein the —COOH group on the anilino ring is located in a position meta or para to the anilino nitrogen.
5. The element of claim 1 wherein the —COOH group on the anilino ring is located in a position para to the anilino nitrogen.
6. The element of claim 1 wherein the —COOH group is located in a position meta to the anilino nitrogen.
7. The element of claim 1 wherein $R_3$ is an aryl group.
8. The element of claim 1 wherein $R_3$ is an alkyl group.
9. The element of claim 8 wherein $R_3$ is selected from alkyl groups having at least 18 carbon atoms.
10. The element of claim 1 wherein Y is selected from the group consisting of alkyl, aryl, amino, oxy, amido, and heterocyclic groups.
11. The element of claim 1 wherein Y is an alkyl group.
12. The element of claim 11 wherein Y is an alkyl group branched at the alpha carbon.
13. The element of claim 1 wherein Y is selected from the group consisting of methyl, ethyl, and phenyl groups.
14. The element of claim 13 wherein Y is methyl.
15. The element of claim 1 wherein X is hydrogen or a coupling-off group.
16. The element of claim 15 wherein X is hydrogen.
17. The element of claim 15 wherein X is a coupling-off group.
18. The element of claim 17 wherein the coupling-off group is selected from the group consisting of halogen, arylthio, aryloxy, and heterocyclic groups.
19. The element of claim 18 wherein the coupling-off group is halogen.
20. The element of claim 1 wherein the coupler has the formula:

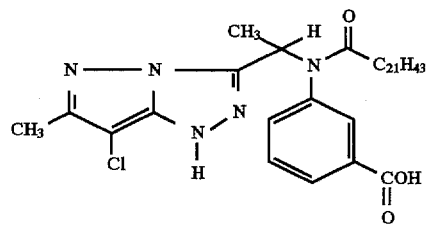

* * * * *